United States Patent [19]

VandenBerg

[11] Patent Number: Plant 6,954

[45] Date of Patent: Jul. 25, 1989

[54] CHRYSANTHEMUM PLANT NAMED CREAM VERO

[75] Inventor: Cornelis P. VandenBerg, Salinas, Calif.

[73] Assignee: Yoder Brothers, Inc., Barberton, Ohio

[21] Appl. No.: 210,003

[22] Filed: Jun. 22, 1988

[51] Int. Cl.[4] ..... A01H 5/00

[52] U.S. Cl. ..... Plt./74

[58] Field of Search ..... Plt./78, 74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Cream Vero particularly characterized by its flat capitulum form; daisy capitulum type; light yellow to cream ray floret color; diameter across face of capitulum of up to 9 cm at maturity; uniform nine week photoperiodic flowering response to short days; medium plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora,* and referred to by the cultivar name Cream Vero.

Cream Vero, identified as 81-064F02, is a product of mutation induction program which had the objective of creating new Chrysanthemum cultivars that would expand the color range of an existing cultivar while retaining all other traits.

Cream Vero was discovered and selected by Cornelis P. VandenBerg on Dec. 18, 1985 in a controlled environment in Salinas, Calif., as one flowering plant within a flowering block established as rooted cuttings from stock plants which had been exposed as unrooted cuttings to an X-ray source of 1500 rads. The irradiated parent was the cultivar identified as Vero, disclosed in pending Plant Pat. application Ser. No. 005,762.

The first act of asexual reproduction of Cream Vero was accomplished when vegetative cuttings were taken from the initial selection in March 1986 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Cream Vero are firmly fixed and are retained through successive generations of asexual reproduction.

Cream Vero has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Cream Vero, which, in combination, distinguish this Chrysanthemum as a new and distinct cultivar:

1. Flat capitulum form.
2. Daisy capitulum type.
3. Light yellow to cream ray floret color.

4. Diameter across face of capitulum up to 9 cm at maturity.
5. Uniform nine week photoperiodic flowering response to short days.
6. Peduncle length ranging from 15 to 20 cm on open terminal sprays.
7. Medium plant height, requiring two long day weeks prior to short days to attain a flowered plant height of 100 to 110 cm for year-round flowerings.
8. Excellent tolerance to low temperatures for bud initiation and flower development.

The accompanying photographic drawings show typical inflorescence and leaf characteristics of Cream Vero, with the colors being as nearly true as possible with illustrations of this type.

Sheet 1 is a color photograph of Cream Vero grown as a single stem cut spray mum.

Sheet 2 is a black and white photograph of three views of the inflorescence of Cream Vero.

Sheet 3 is a black and white photograph showing the upper and under sides of the leaves of Cream Vero at three stages of development (mature, intermediate ad immature).

Of the commercial cultivars known to the inventor, the most similar in comparison to Cream Vero is the parent cultivar Vero. All traits of Cream Vero are similar to those of Vero, except the color of the ray florets. The ray florets of Cream Vero are light yellow to cream in color, whereas Vero has white ray florets.

In the following description, color references are made to The Royal Horticultural Society Colour Chart. The color values were determined on plant material grown as a single stem cut spray mum in Salinas, Calif. on Oct. 14, 1987.

Classification:

*Botanical.*—*Dendranthema grandiflora,* cv Cream Vero.

*Commercial.*—Daisy cut spray mum.

INFLORESCENCE

A. Capitulum:

*Form.*—Flat.

*Type.*—Daisy.

*Diameter across face.*—Up to 9 cm at maturity.

B. Corolla of ray florets:

*Color (general tonality from a distance of three meters).*—Light yellow to cream.

*Color (upper surface).*—5D.

*Color (under surface).*—2D.

*Shape.*—Straight, flat, oblong.

C. Corolla of disc florets:

*Color (mature).*—Closest to 12A to 12B.

*Color (immature).*—Closest to 144A to 144B.

D. Reproductive organs:

*Androecium.*—Present on disc florets only; scant to moderate pollen.

*Gynoecium.*—Present on both ray and disc florets.

PLANT

A. General appearance:

*Height.*—Medium; 100 to 110 cm as a single stem cut mum with two long day weeks prior to short days.

B. Foliage:

*Color (upper surface).*—137A.

*Color (under surface).*—137B.

*Shape.*—Lobed and slightly serrated.

I claim:

1. A new and distinct Chrysanthemum plant named Cream Vero, as described and illustrated.

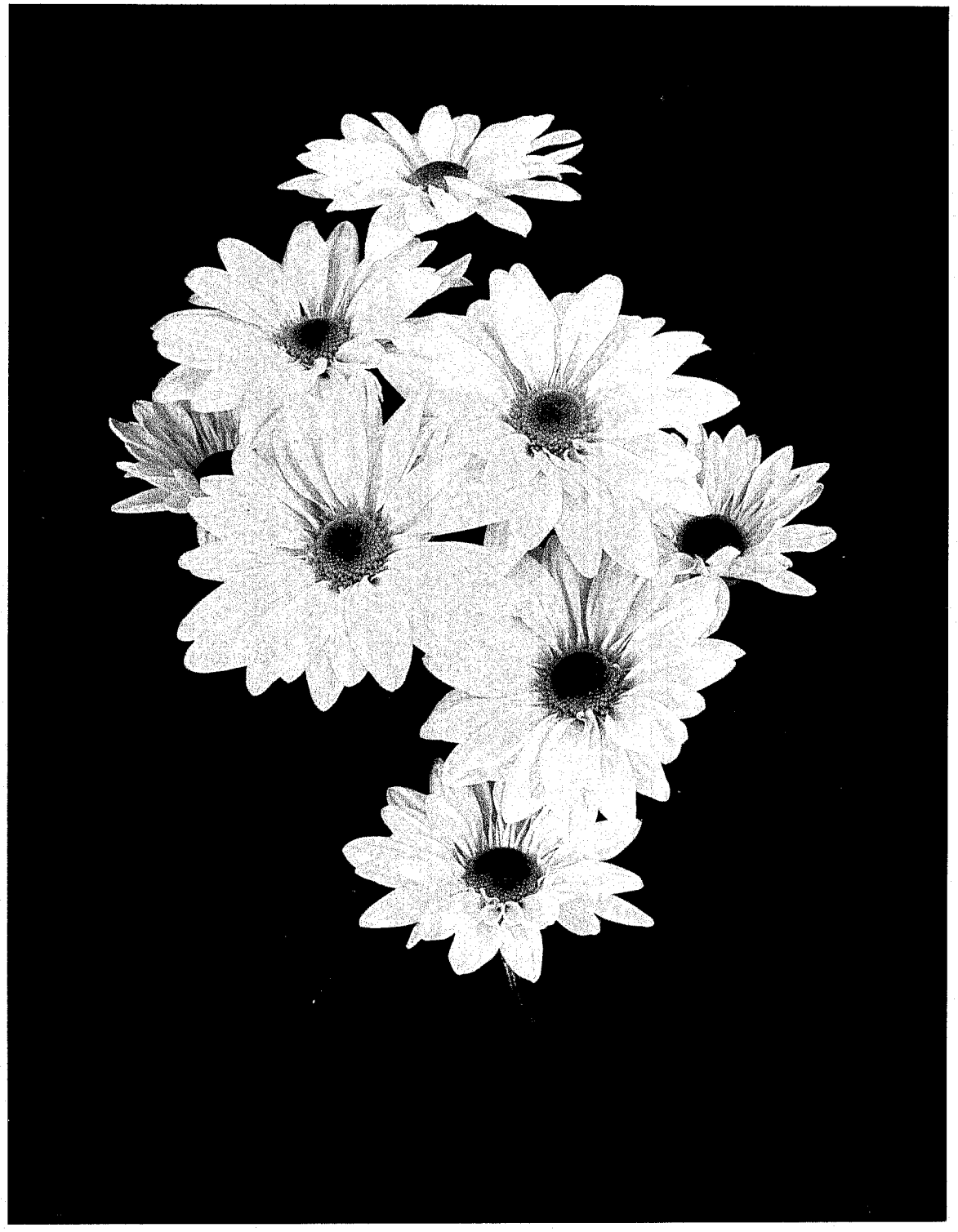

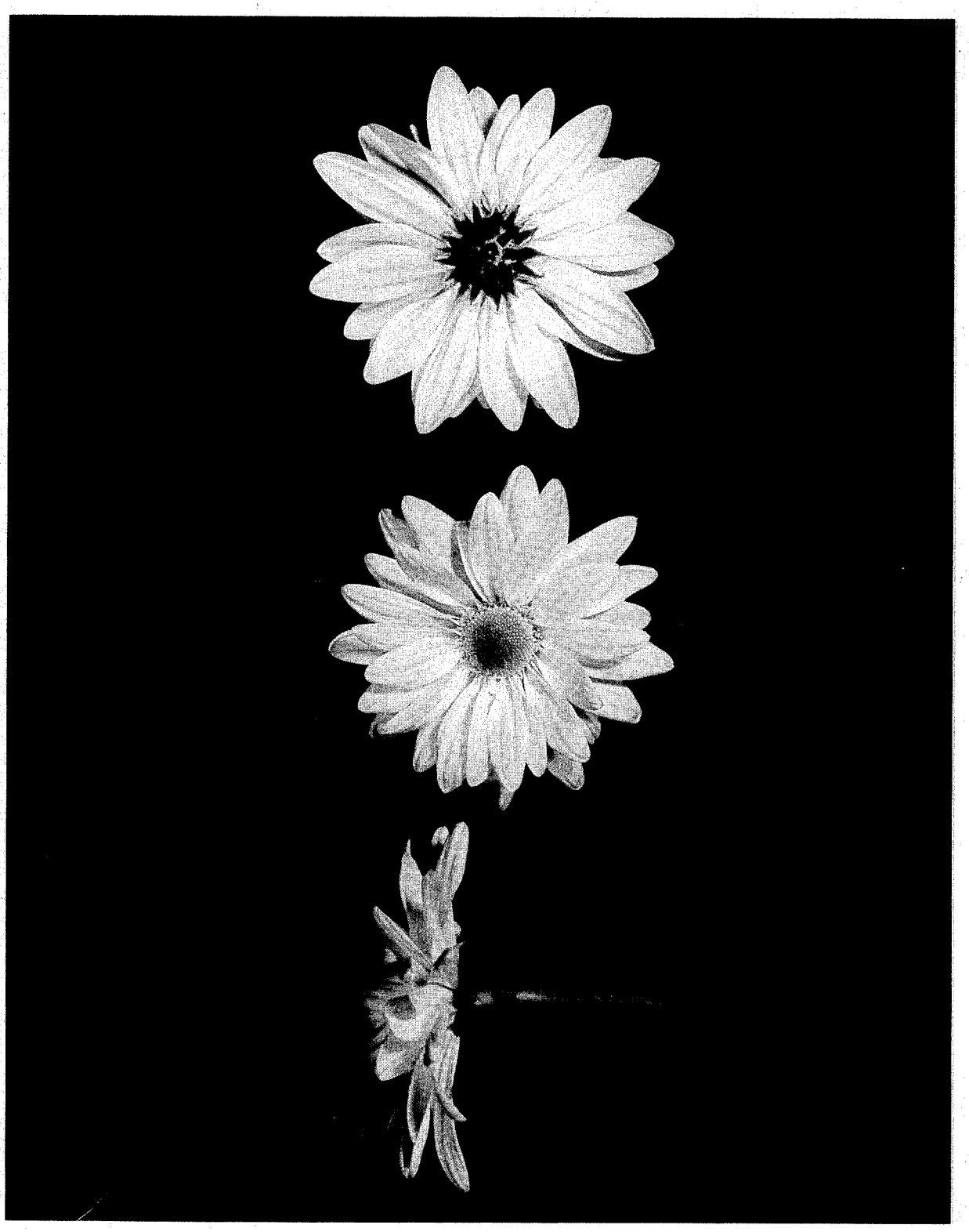

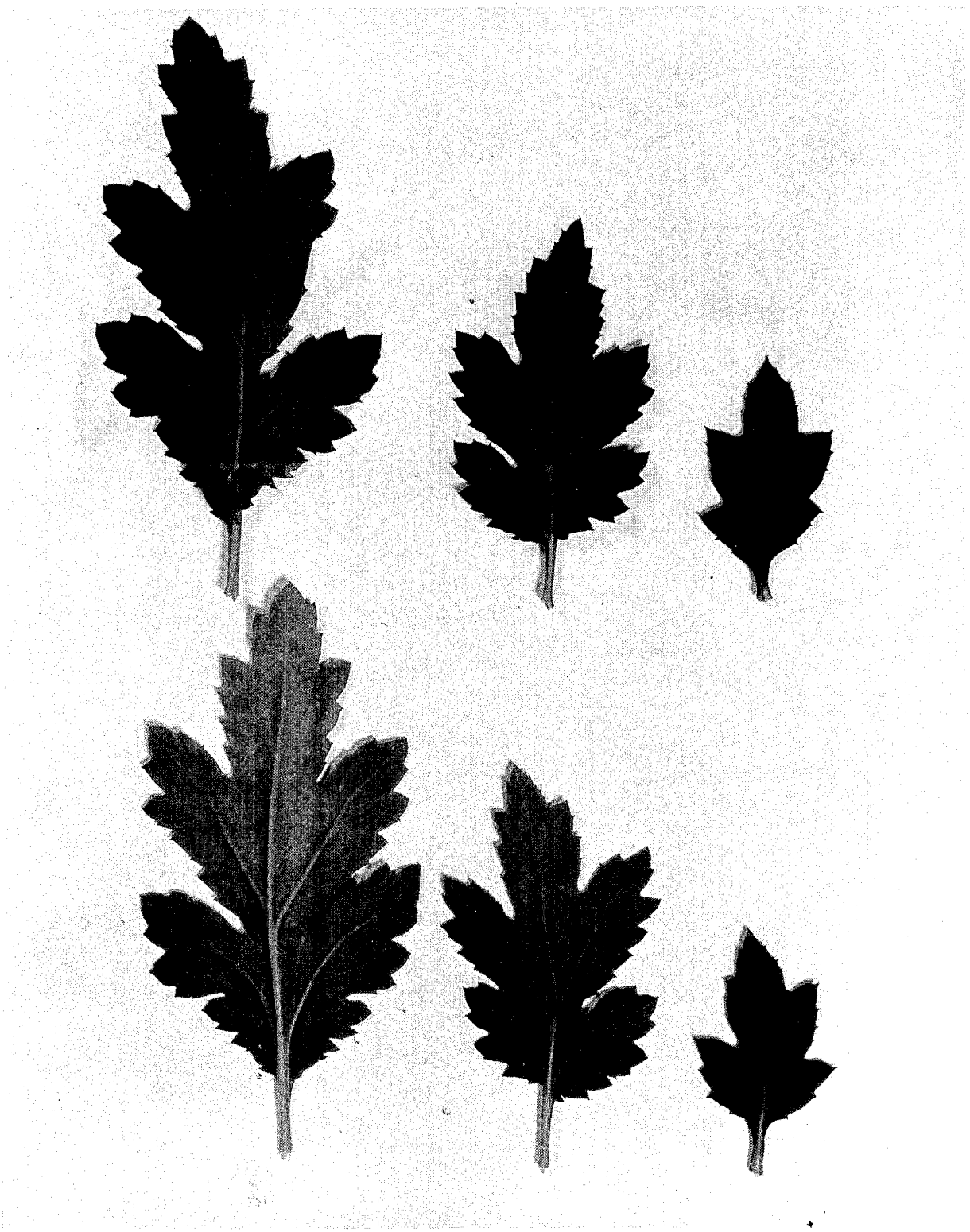

* * * * *